United States Patent [19]

Herrick

[11] Patent Number: 4,910,758
[45] Date of Patent: Mar. 20, 1990

[54] X-RAY DIFFRACTION METHOD FOR GENERATING MINERALOGY RECORD OF WHOLE CORE

[75] Inventor: David C. Herrick, Broken Arrow, Okla.

[73] Assignee: Amoco Corporation, Chicago, Ill.

[21] Appl. No.: 230,207

[22] Filed: Aug. 9, 1988

[51] Int. Cl.⁴ .......................................... G01N 23/207
[52] U.S. Cl. ......................................... 378/71; 378/82; 378/83
[58] Field of Search ................... 378/71, 82, 83, 5, 70

[56] References Cited

U.S. PATENT DOCUMENTS

| 4,076,981 | 2/1978 | Sparks et al. | 378/71 |
| 4,710,946 | 12/1987 | Hinch et al. | 378/62 |
| 4,715,053 | 12/1987 | Comstock et al. | 378/71 |

FOREIGN PATENT DOCUMENTS

| 0104747 | 8/1980 | Japan | 378/71 |
| 0178650 | 8/1986 | Japan | 378/71 |
| 1293593 | 2/1987 | U.S.S.R. | 378/71 |

OTHER PUBLICATIONS

American Instruments, Inc., Promotional Literature, "The Eagle has Landed", Inel CPS-120 System, Received 8-9-88.

Instrumentation Electronique Promotional Literature Relating to CPS 120 System, received 8-9-88.

*Primary Examiner*—Carolyn E. Fields
*Assistant Examiner*—David P. Porta

[57] ABSTRACT

A mineralogical record of whole core is produced by translating whole core relative to a X-ray diffraction source and detector and summing the resulting X-ray diffraction spectra from various surface portions of the core over an interval of the core.

15 Claims, 5 Drawing Sheets

X-RAY DIFFRACTION METHOD FOR GENERATING MINERALOGY RECORD OF WHOLE CORE

FIELD OF THE INVENTION

The invention relates to mineralogical analysis of cores removed from well boreholes. In one aspect, the invention is specially adapted for handling large quantities of core. In a further aspect, the invention relates to using X-ray diffraction spectrometry for nondestructively generating a mineralogy record of whole core. In yet a further aspect, the invention relates to rapidly producing a visual record of the mineralogy of formations intersected by a borehole over a significant length of core.

SETTING OF THE INVENTION

During drilling of wells, special coring bits and core barrels are frequently used to take core along substantially an entire interval of penetration. The core is then visually examined and portions subsequently analyzed for indicia of the presence of oil and gas.

It is useful to preliminarily analyze the core at least sufficiently to show which portions of the core should be subjected to a more detailed analysis and to provide information useful in correlating data from the well with information obtained from other sources. A mineralogy record of the core is useful for both purposes.

One way of obtaining a mineralogy record of core might be to use X-ray diffraction to identify the various minerals encountered. Previous methods of measuring mineralogy using X-ray diffraction, however, are destructive of the core, time consuming, and require extensive laboratory handling of the core which are inconsistent with handling large quantities of core, and more particularly, with handling such large quantities at the well site.

SUMMARY OF THE INVENTION

In accordance with the invention there is provided a nondestructive method using X-ray diffractometry for generating a mineralogical record of whole core taken from a wellbore. The method comprises providing a core taken from a wellbore and successively X-ray irradiating various surface portions of the core producing from the irradiated various surface portions diffracted X-ray radiation at diffracted angles characteristic of minerals present. The intensity of diffracted X radiation from the irradiated various surface portions is measured as a function of diffraction angles. Then, the resulting measures of intensity as a function of diffraction angles from the irradiated various surface portions are summed. The steps of successively irradiating various surface portions, measuring, and summing are continued over sufficient various surface portions of the core for providing an X-ray diffraction spectrum of the core representative of the average mineralogy of the core.

According to a further aspect of the invention, an indicator of mineralogical type is assigned to peaks of the thus summed measures and the assigned indicators are displayed as a function of position along the core.

According to a further aspect of the invention, there is provided apparatus for performing a method in accordance with the invention.

DETAILED DESCRIPTION OF THE INVENTION

Figure 1:
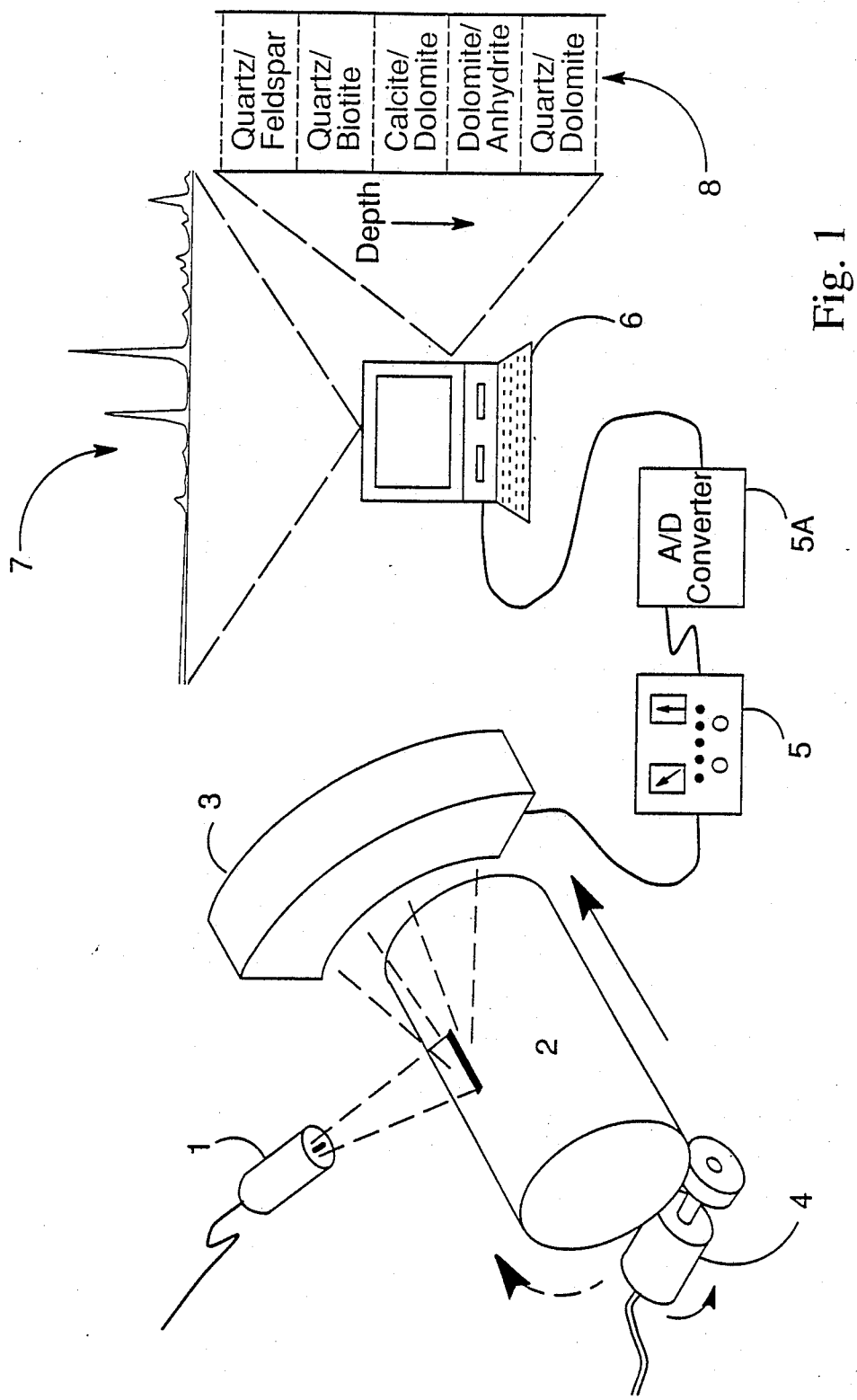
FIG. 1 illustrates method and apparatus in accordance with the invention.

An analytical tool sometimes used for mineralogical analysis of powdered core in the laboratory is X-ray diffraction (XRD). Typical laboratory installations are simultaneously large, heavy, cumbersome, and delicate; and typical laboratory procedures are time-consuming, and as such are not amenable to field applications or to the mineralogical analysis of large quantities of core. While newer XRD apparatus such as multidetector arrays and small X-ray sources eliminate some the the size, weight, and delicacy problems associated with previous instrumentation, XRD for mineralogical analysis conventionally requires that the sample consist of a uniformly finely-ground powder having randomly oriented grains. The powder must be placed into a holder such that the powder has a flat surface. Such preparation of powdered samples from core is time intensive and destructive of the core from which the sample is taken.

A whole core surface, even a cleaned whole core surface, does not meet the conventional requirements of random orientation and uniform size and large number of crystal grains. In using the powder method, the large numbers of randomly oriented and uniformly ground crystal grains are considered necessary to provide sufficient intensity of diffracted radiation at diffraction angles characteristic of mineral(s) present to produce useful XRD spectra. In whole core, to the contrary, the surface is curved, the mineral grains (crystals) may be of virtually any size, and their orientations are frequently not random.

In accordance with the invention, XRD is applied nondestructively for mineralogical analysis of the surface of preferably cleaned whole core in a way suitable for field application and/or for rapid mineralogical analysis of large quantities of core.

The effect of irradiating only a few relatively large nonrandomly oriented crystals is minimized by moving the core relative to the source and detector system during analysis and then integrating the total diffracted X-ray energy over some predetermined length of core (for example, over an interval from 1–10 ft). The movement of the core during analysis greatly increases the number of mineral grains utilized in the analysis, thereby having an effect similar to increasing the number of grains and the randomness of their orientation by the grinding process used in conventional laboratory XRD mineralogical analysis.

In accordance with the invention, an X-ray source irradiates a surface portion of the core and the intensities of diffracted radiation are determined over a range of diffraction angles (theta). By moving the core relative to the source and detector, other surface portions of the core are sampled. By summing and/or averaging the detected diffracted radiation over sufficient such samples, a composite summed set of measurements is achieved which is representative of the average mineralogy of the portion of core being analyzed.

In accordance with the invention, various surface portions of the core are X-ray irradiated and the resulting diffracted X-rays are detected. It will be appreciated that the various surface portions can comprise a continuum along the surface where the core is continually in motion relative to the X-ray source and detector or can comprise discrete portions of the surface where the core is moved in increments or where the X-ray irradiation and diffraction detection occurs at intervals. The discrete portions can be overlapping or nonoverlapping on the surface of the core. It will likewise be appreciated that X-ray irradiation and diffraction detection of various discrete surface portions can grade into X-ray irradiation and diffraction detection of various continuous surface portions.

Referring now to FIG. 1, FIG. 1 illustrates a preferred embodiment of the invention. The apparatus comprises an X-ray source 1 mounted adjacent a curved position sensitive detector 3. A core 2 taken from a wellbore is cause to move by drive means 4 relative to the source 1 and detector 3. The whole apparatus can be effectively shielded with thin sheet metal (not shown) to prevent the escape of X-rays. Unlike conventional laboratory XRD equipment, there are no moving parts in the XRD portion of the apparatus of the preferred embodiment, making the installation relatively simple and amenable to field use.

The X-ray source can be any X-ray source suitable for irradiating various portions of the surface of the core during relative movement of the source and the core. Preferably, the X-ray source can be a commercially available source producing a collimated beam of X-ray irradiation. The X-ray irradiation can be passed through a slit to form a beam of X-ray irradiation which is longer than wide and where the lengthwise direction is parallel to the longitudinal axis of the core being analyzed. Such X-ray sources are readily commercially available and need not be further described here.

The core surface is the limiting factor to successful mineralogical analysis. The effect of the curvature of the surface can be minimized by utilizing an X-ray beam collimated so that it irradiates only a narrow strip of the curved core surface parallel to the length of the core as illustrated in FIG. 1.

The invention is described primarily in terms of its application to whole core which is generally cylindrical in shape having a curved outer surface. It is apparent, however, that the invention, its benefits, and advantages can also be obtained using other types of core samples, for example, slabbed core having a generally planar surface.

In any event, the core surface is preferably cleaned, for example, with brush and water, water jets, and the like to remove traces of drilling fluids, cuttings, and the like. The resulting core surface is relatively smooth, clean, and generally continuous.

In accordance with the invention, the movement of the core relative to the source and the detector can be accomplished by translating the core along its longitudinal axis adjacent the source and detector so that X radiation diffracted from various surface portions of the core is effectively received by the detector. Other forms of motion can also be accomplished, for example, the movement can be in discrete increments or continuous; the movement can be parallel to the longitudinal axis or can be by rotating the core around its longitudinal axis, or by combinations of both movements. By rotating the core around its longitudinal axis, a larger area of various surface portions per unit length will be sampled by the apparatus. Generally, simple linear motion in a direction parallel to the longitudinal axis will be sufficient.

The radiation diffracted from the various surface portions of the core is sensed by the detector 3 which produces a measure of intensity of diffracted radiation as a function of diffraction angle across a range of diffraction angles.

Preferably, the X-ray detector comprises a curved multiposition detector effective for concurrently sensing the intensity of diffracted radiation over a wide angular range of diffraction angles (theta). For example, the CPS 120 System Curved Position Sensitive Detector available from Instrumentation Electronique, Buc, France, can be used. The CPS 120 is effective for concurrently sensing the intensity of diffracted radiation across a 120° two theta angular range and for producing an output signal representative of the intensity of diffracted radiation as a function of angular position. Alternatively the X-ray detector can comprise an array of detectors positioned at detection angles corresponding to the major minerals of interest.

As the core is moved and various surface portions of the core are irradiated and resulting diffraction measured, the resulting measures are analyzed by analyzer preferably provided with an analog-to-digital converter 5a and the digitized signals can be provided to computer 6.

Thus, in the analyzer with a/d converter, the measures representative of diffracted X-ray peak position as a function of diffraction angle can be electronically analyzed and digitized and stored in memory as the various surface portions of core surface are scanned.

The analyzer can be a commercially available multichannel analyzer and the analog-to-digital converter can be a suitable analog-to-digital converter such as are commercially available for use with such analyzers. A suitable analyzer for use with the invention is the American Instruments Data Handling Electronic Package available from American Instruments Inc., Port Reading, NJ.

Those skilled in the art of X-ray diffractometry will appreciate that the measures from the various portions of the core's surface are far from providing a useful mineralogical record of the core. Diffraction patterns from each various portion is characterized by relatively few crystals and by typically nonrandom orientation in comparison with the typical prepared powder specimen. In accordance with the invention, the measures from the various surface portions are summed and the steps of irradiating various surface portions, measuring, and summing are continued until sufficient various surface portions have been irradiated, measured, and summed to produce, in effect, an XRD spectrum of the core. Thus the invention overcomes the limitations of whole core relative to the powder technique by sufficiently continuing the steps of irradiating, measuring, and summing over various surface portions of whole core.

As indicated, the summing step can preferably be accomplished by digitizing the measures produced by the analyzer in analog-to-digital converter 5a. The digitized measures can then be summed by the computer. The computer can be a personal computer having sufficient capacity for processing signals in accordance with the invention. Most currently available personal computers will easily meet these requirements.

The summing can be performed over a discrete interval or a running sum over a preselected interval can be generated and maintained.

According to the former, the measures over a discrete interval, for example from a first position to a second position on the core can be generated and summed. According to the latter aspect, after generating such a sum over a discrete interval, additional measures can be summed as they are occurring, while earlier measures over a portion of the core greater than the preselected interval are being dropped from the sum. Averaging and other data processing of the digitized signals and of the summed digitized signals can also be performed by the computer.

Thus, for example, in accordance with the invention, the different crystal structures present in a 1-ft interval can be identified by comparing peaks occurring in the interval with peaks characteristic of the minerals. Then a record using symbolic or other representation can be generated as a function of depth along the core indicating its mineralogical content. Such a record is illustrated schematically by reference 8 in FIG. 1.

According to a further aspect of the invention, the X-ray source and the detector can be stationary while the core moves relative to them.

EXAMPLE

Figure 2A:
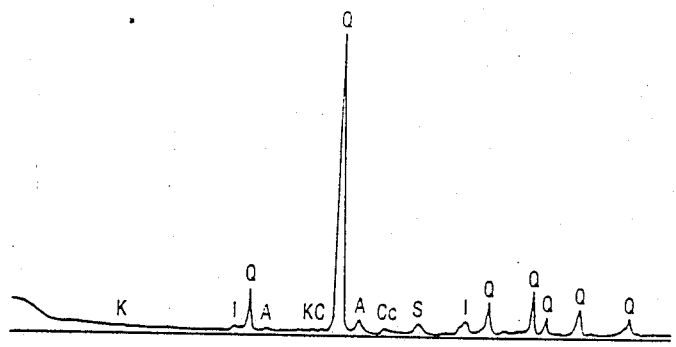
FIGS. 2–4 illustrate results obtainable using the invention.
Figure 2B:
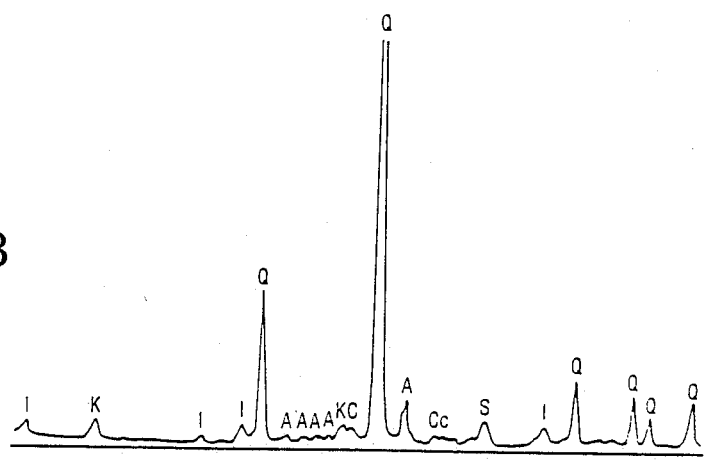
Figure 2C:
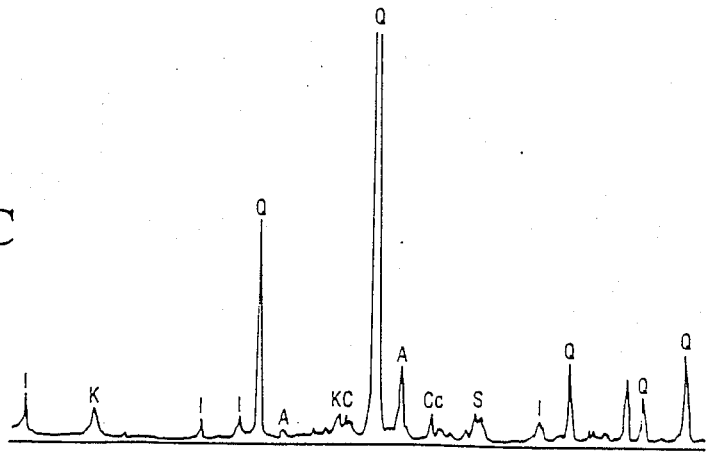
Figure 3A:
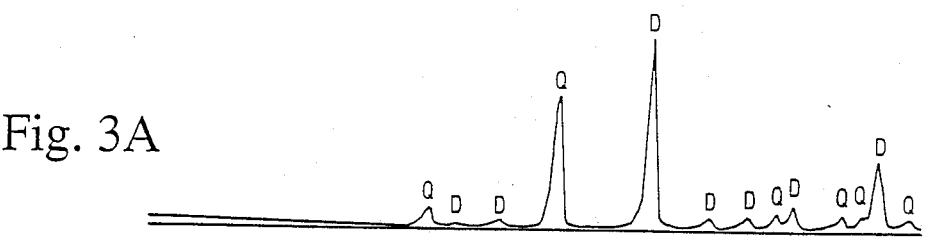
Figure 3B:
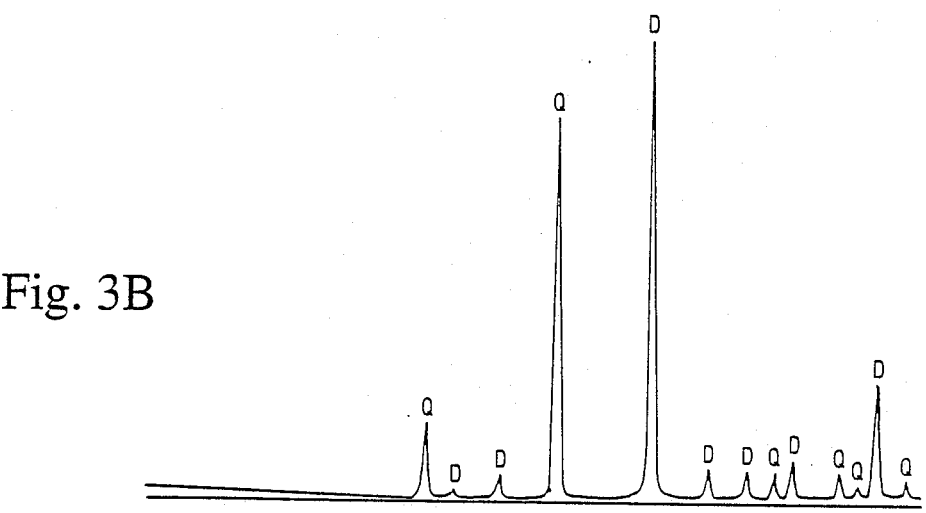
Figure 3C:
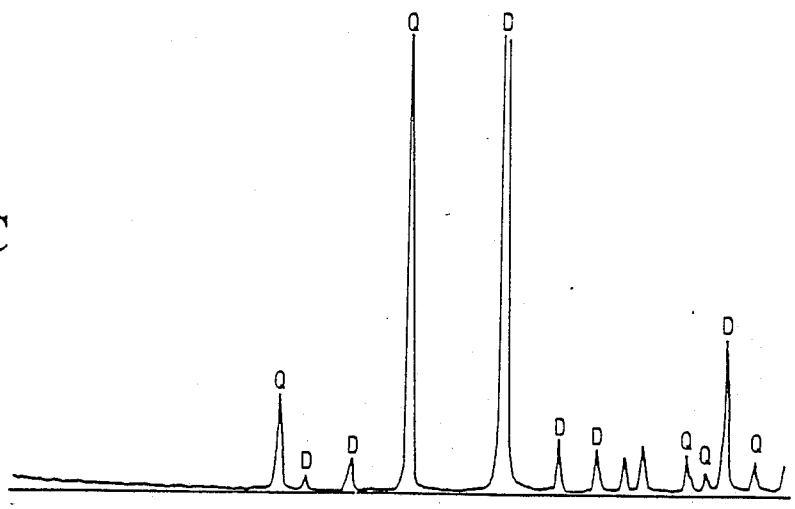
Figure 4A:
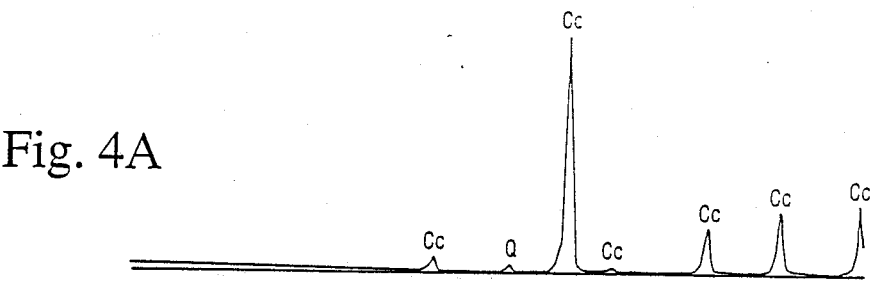
Figure 4B:
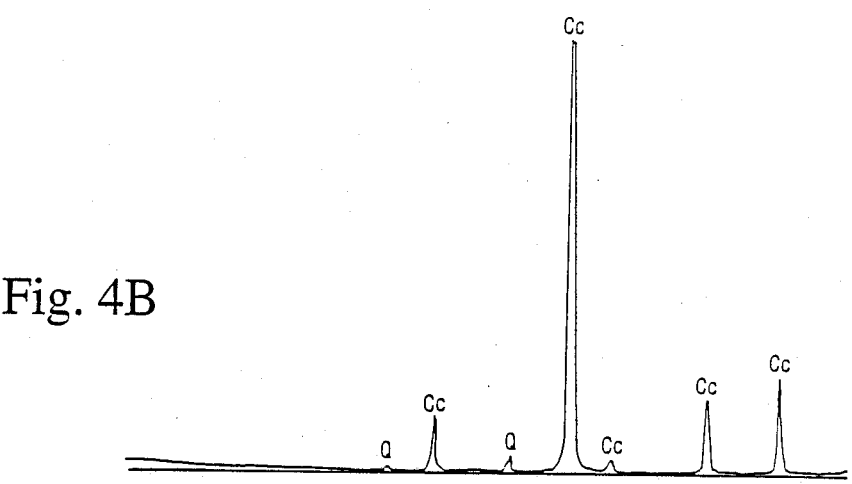
Figure 4C:
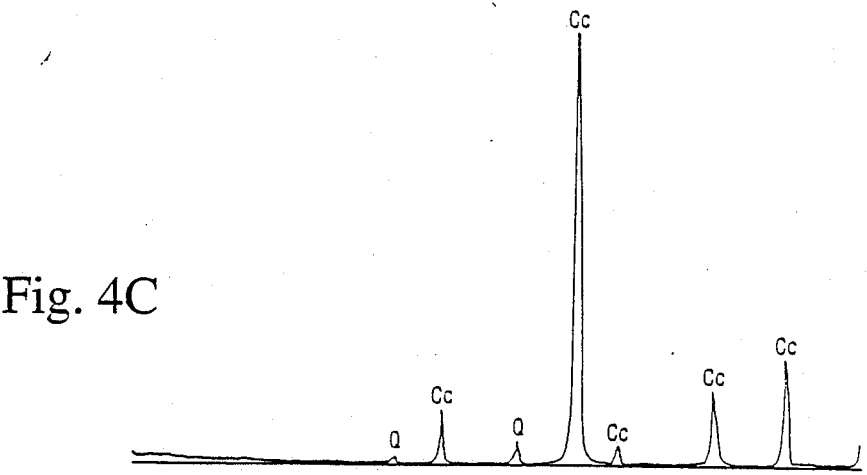
Figure 5A:
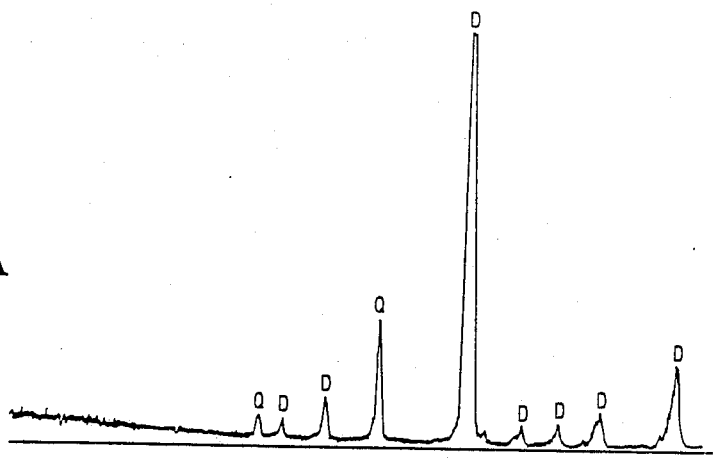
Figure 5B:
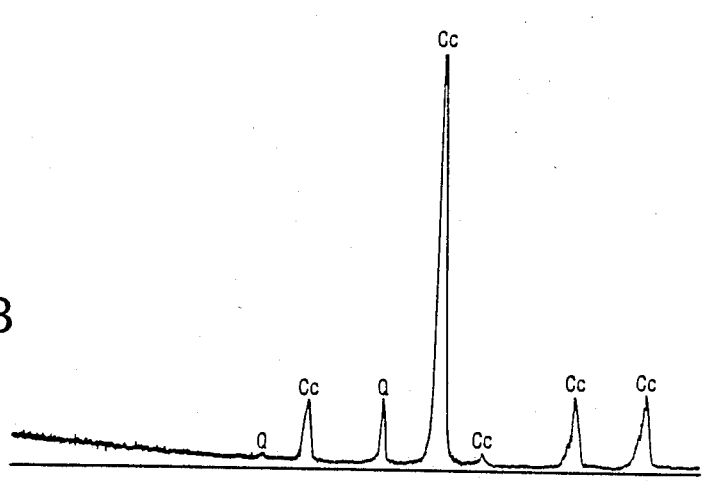
Figure 5C:
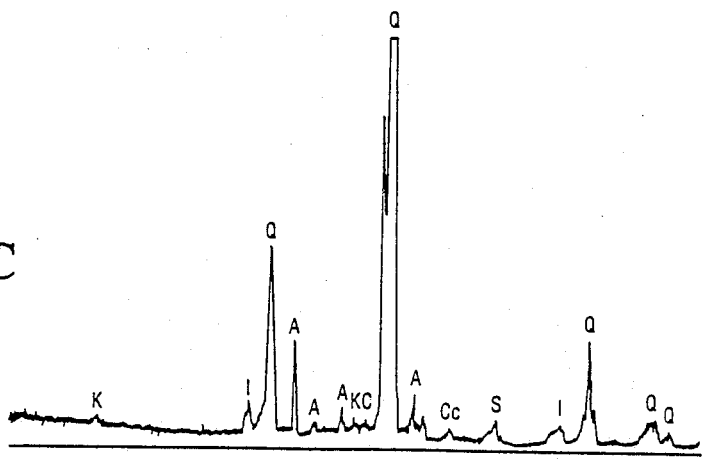

The effectiveness of analyzing and integrating the results of XRD analysis over an entire length of core is investigated by cutting three 1-ft sections of core into 1-in lengths. Using standard laboratory XRD apparatus, a measure of intensity of X-ray diffraction as a function of diffraction angle is obtained from the curved surface of each 1-in sample. The measures from the individual 1-in samples are summed to obtain a spectrum representative of the entire 1-ft length of core. This summed spectrum simulates the spectrum which is obtained by analyzing a moving core in accordance with the invention. The resulting spectra for each of the cores are shown in FIGS. 2-4.

In the figures, the following legends are used: Q-Quartz, Cc-Calcite, I-Illite, A-Albite, K-Kaolinite, C-Chlorite, S-Siderite, and D-Dolomite.

To illustrate that the X-ray diffraction spectra obtained by this technique reflects the mineralogical composition of the core, two additional runs are performed.

First, a portion of each 1-in sample is ground and a powder X-ray diffraction spectrum is obtained in the usual way. The spectra from each 1-in sample for a core are summed and plotted in FIGS. 2-4 in the center spectrum of each figure designated "2. Average of all Powdered Core Samples".

Secondly, the powders of each 1-in sample along a core are all combined, mixed, and subsampled to get a single powder XRD sample representative of the entire core. The diffraction pattern of this composite sample is also shown in FIGS. 2-4 for comparison in the bottom spectrum of each figure designated "3. Composite Powdered Core".

This example indicates that the analysis of the exterior curved surface of a length of core can be accomplished using X-ray diffraction by summing and averaging over the entire length and nevertheless can produce results comparable with those obtained by conventional powder sample methods.

This Example further illustrates that limitations of crystal size, orientation, and variable composition encountered when analyzing a core surface can be overcome by continuous X-ray diffraction analysis of the curved surface of core and by expressing the composition as an average over a predetermined length.

The method in accordance with the invention thus provides a semiquantitative method for nondestructively generating a mineralogical record of whole core. The method can be used, for example, to identify common minerals encountered in core such as quartz, anhydrite, calcite, aluminum silicates, carbonates, dolomites, pyrites, feldspar, siderite, and the like.

The invention also provides significant advantages of time and labor savings. Thus, using a 1-in sample size as in the Example, then for a 1-ft core section, the powdered sample preparation time is about 20 minutes per sample or 4 hrs. per ft. The time required for X-ray diffraction of prepared powder specimens is about 5 minutes per sample (1 hr per ft) where only major mineralogical components are of interest and about 20 minutes per sample (4 hrs. per ft.) for a typical XRD scan rate. By comparison, the rate for mineralogical analysis using the invented method is on the order of a few minutes per ft. of core.

The invention has been illustrated in preferred embodiments and using specific examples. The invention, however, is not limited by these preferred embodiments and by these specific examples but by the claims appended hereto interpreted in accordance with established principals of law.

What is claimed is:

1. A nondestructive method using X-ray diffractometry for generating a mineralogical record of whole core taken from a wellbore comprising:
   providing a core taken from a wellbore;
   successively X-ray irradiating various surface portions of the core producing from the irradiated various surface portions diffracted X-radiation;
   measuring intensity of diffracted X-radiation from irradiated various surface portions as a function of diffraction angles; and
   summing the resulting measures of intensity as a function of diffraction angle from irradiated various surface portions; wherein
   the steps of successively irradiating various surface portions, measuring, and summing are continued over sufficient various surface portions for providing an X-ray diffraction spectrum of the core representative of mineralogy of the core.

2. The method of claim 1 further comprising:
   assigning an indicator of mineralogical type to the peaks of the thus summed measures; and
   displaying the assigned indicators as a function of position along the core.

3. The method of claim 1 wherein the steps of successively X-ray irradiating and measuring comprises:
   providing a source of X-ray irradiation;
   providing a detector of intensity of diffracted X-rays as a function of diffraction angle; and
   moving the core relative to the source and the detector for successively X-ray irradiating and measuring intensity as a function of diffraction angle from various surface portions of the core.

4. The method of claim 3 wherein:
   the core is moved and the source and detector are stationary.

5. The method of claim 3 wherein:
   the core is generally cylindrical in shape having a curved outer surface and a longitudinal axis; and wherein the core is moved relative to the source and detector in a direction parallel to its longitudinal axis.

6. The method of claim 3 wherein:
the core is generally cylindrical in shape having a curved outer surface and a longitudinal axis; and wherein
the core is moved relative to the source and detector by being rotated about its longitudinal axis.

7. The Method of claim 3 wherein:
the core is generally cylindrical in shape having a curved outer surface and a longitudinal axis; and wherein
the core is moved relative to the source and detector by moving the core in a direction parallel to its longitudinal axis, and concurrently rotating the core about its longitudinal axis.

8. The Method of claim 3:
wherein the core is maintained stationary and the source and the detector are moved relative to the core.

9. The method of claim 3:
wherein the core has a generally planar surface which during movement relative to the source and the detector is X-ray irradiated and from which resulting X-ray diffraction is measured.

10. The method of claim 1:
wherein the resulting measures of intensity of diffraction as a function of diffraction angles are summed over discrete, nonoverlapping intervals along the core.

11. The method of claim 1:
wherein the resulting measures of intensity of diffraction as a function of diffraction angles are summed over discrete, overlapping intervals along the core.

12. The method of claim 1:
wherein the resulting measures of intensity of diffraction as a function of diffraction angles are summed over a continuous interval along the core.

13. The method of claim 1:
wherein the resulting measures are summed by producing a running average over a preselected interval along the core.

14. The method of claim 10 comprising:
displaying the plurality of nondiscrete overlapping mineralogical representations of the core in a record as a function of depth.

15. Apparatus for nondestructively using X-ray diffractometry for generating a mineralogical record of whole core taken from a wellbore comprising:
means for successively X-ray irradiating various surface portions of a core in a target zone producing from the irradiated various surface portions diffracted X-radiation;
means for moving a core taken from a wellbore through the target zone for X-ray irradiation and for detection of diffracted X-ray irradiation therefrom;
means for measuring intensity of diffracted X-ray irradiation as a function of diffraction angle from irradiated various surface portions; and
means for summing the resulting measures of intensity as a function of diffraction angle from irradiated various surface portions.

* * * * *